United States Patent
Yoh et al.

(10) Patent No.: US 11,400,219 B2
(45) Date of Patent: Aug. 2, 2022

(54) MICROJET DRUG DELIVERY SYSTEM WITH ENHANCED DRUG PENETRATION PERFORMANCE BY FRACTIONAL LASER PRE-ABLATION

(71) Applicant: SNU R&DB FOUNDATION, Seoul (KR)

(72) Inventors: Jai-Ick Yoh, Seoul (KR); Hun Jae Jang, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 769 days.

(21) Appl. No.: 16/321,168

(22) PCT Filed: Jul. 27, 2017

(86) PCT No.: PCT/KR2017/008102
§ 371 (c)(1),
(2) Date: May 3, 2019

(87) PCT Pub. No.: WO2018/021846
PCT Pub. Date: Feb. 1, 2018

(65) Prior Publication Data
US 2019/0255253 A1 Aug. 22, 2019

(30) Foreign Application Priority Data
Jul. 28, 2016 (KR) .................... 10-2016-0096366

(51) Int. Cl.
*A61M 5/30* (2006.01)
*A61M 5/20* (2006.01)
(Continued)

(52) U.S. Cl.
CPC ................ *A61M 5/30* (2013.01); *A61M 5/20* (2013.01); *A61M 5/2053* (2013.01);
(Continued)

(58) Field of Classification Search
CPC ........ A61M 5/30; A61M 5/20; A61M 5/2053; A61M 5/3007; A61M 5/42; A61M 5/422;
(Continued)

(56) References Cited

U.S. PATENT DOCUMENTS 5,713,845 A 2/1998 Tankovich
5,741,247 A 4/1998 Rizoiu et al.
(Continued)

FOREIGN PATENT DOCUMENTS

JP 2001511668 A 8/2001
KR 1020070018726 A 2/2007
(Continued)

OTHER PUBLICATIONS

E.H. Tauorf et al, Fractional Laser-Assisted Drug Delivery: Laser Channel Depth Influences Biodistribution and Skin Deposition of Methotrexate, Lasers in Surgery and Medicine, Feb. 5, 2016, vol. 48, pp. 519-829, Wiley Periodicals, inc, Hoboken, USA.*
(Continued)

*Primary Examiner* — Theodore J Stigell
(74) *Attorney, Agent, or Firm* — STIP Law Group, LLC (57) ABSTRACT

Disclosed is drug delivery system for effectively administering a drug into a human or animal body tissue. The microjet drug delivery system includes (a) a microjet injector including: a pressure chamber partially sealed by an elastic membrane and containing a pressure-inducing liquid fluid-tightly filled therein; and a drug chamber adjacent to the pressure chamber, wherein the elastic membrane is disposed between the pressure and drug chambers, wherein the drug solution is contained in the drug chamber, wherein the drug chamber has a micro-nozzle partially defined in a wall thereof for ejecting the drug solution out of the drug chamber; (b) a laser generator for generating a laser beam and emitting the laser beam out of the laser generator,
(Continued)

wherein the laser generator is configured by irradiating the laser beam into the pressure-inducing liquid in the microjet injector, thereby generating a bubble in the pressure-inducing liquid; and (c) a fractional laser filter module configured for splitting the laser beam incident from the laser generator into a plurality of fractional laser beams, each beam has a reduced diameter, and for irradiating the fractional laser beams. According to the microjet drug delivery system, the pre-ablating of the skin with the fractional laser beams to partially remove the stratum corneum may enable the drug microjet based injection to allow the drug to be effectively invaded into a skin tissue at the portion where the stratum corneum is partially removed and relatively softened.

4 Claims, 10 Drawing Sheets

(51) Int. Cl.
  *A61M 5/42* (2006.01)
  *G02B 27/14* (2006.01)
  *H01S 3/16* (2006.01)
  *H01S 3/00* (2006.01)

(52) U.S. Cl.
  CPC ............ *A61M 5/3007* (2013.01); *A61M 5/42* (2013.01); *A61M 5/422* (2013.01); *G02B 27/14* (2013.01); *H01S 3/005* (2013.01); *H01S 3/16* (2013.01)

(58) Field of Classification Search
  CPC . G02B 27/24; H01S 3/005; H01S 3/16; H01S 3/1643; H01S 3/1608
  See application file for complete search history.

(56) References Cited

U.S. PATENT DOCUMENTS

| | | | |
|---|---|---|---|
| 5,999,678 | A | 12/1999 | Murphy-Chutorian et al. |
| 6,641,553 | B1 | 11/2003 | Chee et al. |
| 7,400,940 | B2 | 7/2008 | McRae et al. |
| 8,905,966 | B2 | 12/2014 | Yoh et al. |
| 2002/0045911 | A1 | 4/2002 | Fletcher et al. |
| 2003/0014014 | A1 | 1/2003 | Nitzan |
| 2003/0114789 | A1 | 6/2003 | Haar et al. |
| 2003/0139041 | A1 | 7/2003 | LeClair |
| 2004/0260234 | A1 | 12/2004 | Srinivasan et al. |
| 2009/0129945 | A1 | 5/2009 | Adleff et al. |

FOREIGN PATENT DOCUMENTS

| | | | |
|---|---|---|---|
| KR | 1020110104409 A | | 9/2011 |
| KR | 101430365 B1 | | 8/2014 |
| KR | 1020150100105 | * | 9/2015 |
| KR | 1020150100105 A | | 9/2015 |

OTHER PUBLICATIONS

Jeanne C. Stachowiak et al, Piezoelectric control of needle-free transdermal drug delivery, ScienceDirect, Aug. 23, 2007, vol. 124, pp. 88-97, Elsevier Inc, Atlanta, USA.

Viren Menezes et al, Shock wave driven liquid microjets for drug delivery, Journal of Applied Physics, Oct. 26, 2009, vol. 106, pp. 086102-1 to 086102-3, American Institute of Physics, College park, USA.

Tae-Hee Han et al, Drug injection into fat tissue with a laser based microjet injector, Journal of Applied Physics, May 5, 2011, vol. 109, pp. 093105-1 to 093105-3, American Institute of Physics, College park, USA.

E.H. Tauorf et al, Fractional Laser-Assisted Drug Delivery: Laser Channel Depth Influences Biodistribution and Skin Deposition of Methotrexate, Lasers In Surgery and Medicine, Feb. 5, 2016, vol. 48, pp. 519-529, Wiley Periodicals, Inc, Hoboken, USA.

Tae-Hee Han et al, A laser based reusable microjet injector for transdermal drug delivery, Journal of Applied Physics, May 27, 2010, vol. 107, pp. 103110-1 to 103110-3, American Institute of Physics, College park, USA.

Woan-Ruoh Lee et al, Skin pretreatment with an Er:YAG laser promotes the transdermal delivery of three narcotic analgesics, Lasers Med Science, Mar. 3, 2007, vol. 22, pp. 271-278, Springer-Verlag London Limited, London, United Kingdom.

G. N. Sankim & P. Zhong, Interaction between shock wave and single inertial bubbles near an elastic boundary, NIH-PA Author Manuscript, Aug. 13, 2007, 74(4 Pt 2):046304, Phys Rev E Stat Nonlin Soft Matter Phys, National Institute of Health, Bethesda, USA.

International Search Report of PCT/KR2017/008102, dated Nov. 24, 2017, English translation.

\* cited by examiner

MICROJET DRUG DELIVERY SYSTEM WITH ENHANCED DRUG PENETRATION PERFORMANCE BY FRACTIONAL LASER PRE-ABLATION

CROSS-REFERENCE TO RELATED APPLICATIONS

This application is the U.S. National Phase under 35 U.S.C. § 371 of International Application No. PCT/KR2017/008102 filed on Jul. 27, 2017, which in turn claims the benefit of Korean Application No. KR 10-2016-0096366, filed on Jul. 28, 2016, the disclosures of which are incorporated by reference into the present application.

TECHNICAL FIELD

The present disclosure relates to a drug delivery system for effectively administering a drug into a human or animal body tissue. More specifically, the present disclosure relates to a microjet drug delivery system capable of quickly and easily administering a drug in the body while reducing a pain during injection, by ejecting the drug in a high-speed microjet form to inject the drug into the tissue without an injection needle.

RELATED ART

Generally, in a medical field, a drug delivery system for administering a therapeutic drug in a patient's body may be divided into an oral administration system and a parenteral administration system. The most commonly used approach in the parenteral drug delivery system is conventionally a needle syringe based approach. However, the conventional needle-type syringe as described above causes a major pain at a time of injection of the needle. In addition, there is a risk of infection due to a wound caused by the needle. Further, the needle syringe should be discarded because it could not be reused for hygiene reasons.

Due to the shortcomings of the conventional needle-type syringe, development of needle-free drug delivery systems as a substitute for the needle-type syringe has been widely researched. In an attempt to develop the needle-free drug delivery system, there has been proposed a drug delivery system of ejecting a drug solution in a form of a microjet having a micro diameter at a high speed and allowing the drug solution to be directly penetrated into an internal target spot through epidermis.

In the microjet drug delivery system, in order to produce a high-speed drug microjet, a strong propulsion force is applied (directly or indirectly) onto the ejected drug, so that the drug is forced out externally through a micro-nozzle orifice. In this microjet drug delivery system, the propulsion force generation approach has been variously developed since 1930s. Various ejection methods have been developed as follows. Until recently, piezoelectric ceramics were used for ejection. Alternatively, an ejection method using a shock wave induced by applying a laser beam to an aluminum foil, a method using a compression spring or a compressed gas, or an ejection method using Lorentz force has been employed.

In recent years, unlike the conventional microjet ejection methods, a laser-bubble type microjet ejection has been developed by the present applicant. In this laser-bubble type microjet ejection, the amount of ejected drug and the ejection rate (i.e. drug penetration depth) may be finely adjusted, and continuous injection and reusability may be achieved.

This laser-bubble type technique has been filed as Korean Patent Application No. 10-2010-56637 (titled "microjet drug delivery system"). The above patent application is patented as KR patent number 1207977.

FIG. 10 shows a laser-bubble type microjet drug delivery device as described in the above-mentioned patent document. FIG. 10a shows a state before the ejection of the drug, and FIG. 10b shows a state where the drug is ejected. Referring to FIG. 10, the microjet drug delivery device described in the above patent document includes a pressure chamber 10 having a pressure inducing liquid hermetically filled therein, a drug chamber 20 disposed adjacent to the pressure chamber 10 to store a drug solution therein, an elastic membrane 30 disposed between the pressure chamber 10 and the drug chamber 20 to partition the pressure chamber and the drug chamber, and an energy focusing unit 40 configured to apply strong energy of a laser beam or the like onto an inner portion of the pressure chamber 10 to change the pressure inducing liquid from a gas state to a liquid state.

According to the above-described microjet drug delivery device as described in the above patent document, when the energy focusing unit 40 irradiates the pressure inducing liquid 100 into the pressure chamber 10 with the strong energy of the laser beam or the like in a concentrated manner, the pressure inducing liquid 100 evaporates momentarily, thus, a bubble is generated therein. Then, during rapid expansion and disappearance of the generated bubble, the elastic membrane 30 is expanded. Due to the expansion of the elastic membrane, the drug solution in the drug chamber 20 is rapidly pressured and ejected through the nozzle, so that the microjet of the drug solution is injected at an enough speed to penetrate soft tissue of the body.

In the microjet-based patented microjet drug delivery system as described above, the drug jet loses kinetic energy during penetrating the skin tissue, and, thus, inevitably, the jet speed deceleration occurs and the skin invasion depth becomes insufficient. Particularly, a stratum corneum defining the outermost layer of the skin has a thickness of about 50 to 100 um, and thus is relatively stronger than other underlying skin tissues. Thus, the stratum corneum blocks invasion of foreign matter from the outside. Thus, when administering a microjet, the drug jet is blocked by the stratum corneum. Further, a splash-back phenomenon occurs because the jet speed and the skin erosion speed of the drug are different. As a result, not only the efficiency of drug invasion is greatly reduced, but also there is a problem of secondary infection.

Therefore, the present disclosure aims to solve the problems about the conventional microjet-based drug delivery system as described above. In accordance with the present disclosure, a combination of a laser skin ablation module and a microjet injector may improve skin invasion performance of the drug jet and drug delivery efficiency via pre-ablation of the skin tissue before administering the drug jet.

Figure 7:
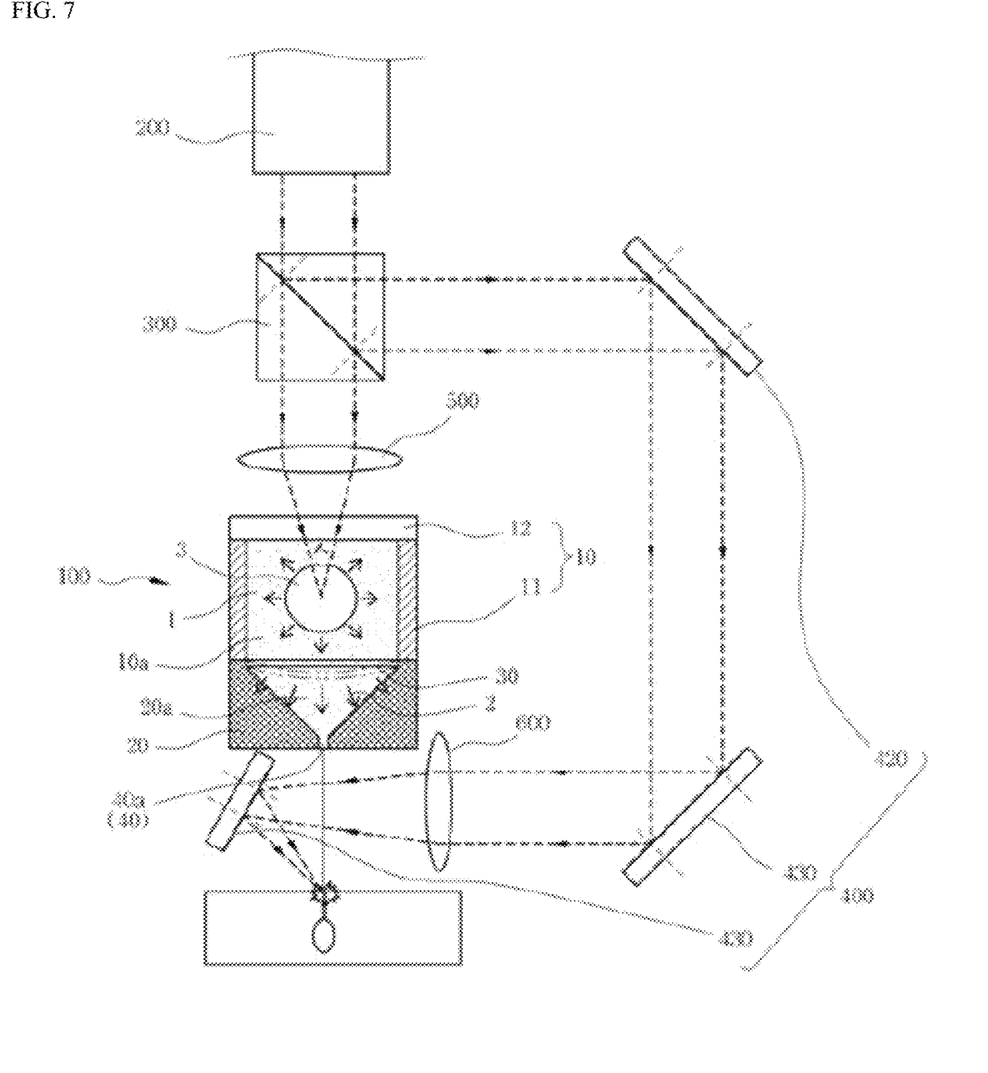
FIG. 7 is a view showing a structure of a conventional patented laser-bubble based microjet drug delivery device equipped with a beam splitter.

In this regard, the present inventor has improved the conventional patented microjet drug delivery system. As shown in FIG. 7, a portion of the laser irradiated to the microjet injector is branched via a newly designed beam splitter member. This branched laser portion is applied to a drug injection portion of the skin to remove epidermis therein and then microjets are ejected to the portion. Thus, the present inventor has developed a microjet drug delivery system that can efficiently inject drugs into the skin dermal layer. This invention was filed as a Korean patent application 10-2014-0021473 titled "microjet drug delivery device and drug delivery method using the same" which was patented as Korean Patent No. 10-154996.

According to the patented invention of the present inventor as described above, injecting a drug in a microjet form into a portion of the skin where the epidermis of the skin is removed by a laser may allow injecting the drug efficiently into the dermis in the skin via microjet ejection. However, for the patented invention, since the laser beam is branched and a portion of the branched beam is irradiated to the skin and at the same time the remaining beam is irradiated to the microjet injector, entire laser energy has not been used for the microjet propulsion, thereby causing the microjet speed to drop in spite of the same laser power.

Further, according to the above patented invention, when laser is applied to the drug to-be-administered portion of the skin, the laser is focused on a narrow portion of the skin surface via a lens. Thus, there were many difficulties in precisely aligning the microjet path to this skin ablated portion.

In addition, for the above patented invention, as the laser is directly focused on the skin, the damage of the skin is severe, leading to burn and infection. After the microjet injection treatment, it took a long time to heal the skin.

DISCLOSURE OF INVENTION

Technical Purpose

Accordingly, the present disclosure has been made in order to solve the problems of the conventional microjet-based drug delivery system as described above. An purpose of the present disclosure is to provide a microjet drug delivery system capable of effective drug delivery, in which the system includes a fractional laser filter module to ablate the stratum corneum of the skin prior to the microjet injection, and then the microjet drug is injected into the ablated portion of the skin while aligning the microjet ejection path thereto, thereby to effectively invade the drug through the relatively soft skin tissue into the body and to inhibit the splash-back phenomenon.

Further, the present disclosure has been made in order to solve the problem of the skin damage and long healing time due to the skin laser pre-irradiation. Thus, another purpose of the present disclosure is to provide a microjet drug delivery system, in which the skin pre-ablation, an output laser is split into multiple fractional lasers of micro-diameters which in turn are irradiated to the skin, resulting in a low skin damage and low side effects during skin regeneration and healing periods.

Furthermore, the present disclosure has been made in order to solve the problem of the difficulty in aligning the microjet path to the ablated portion during skin ablation pre-treatment. Thus, still another purpose of the present disclosure is to provide a microjet drug delivery system, in which allowing the laser to perforate the skin while rotating the fractional laser filter module at a predetermined angular spacing may allow the spacing between the skin holes to be smaller and allow increasing the number of holes per unit area, thereby to greatly increase the likelihood of aligning the microjet paths to the skin holes generated via the fractional laser beams.

Technical Solutions

Regarding technical solutions to accomplish the above purposes, the present disclosure provides a microjet drug delivery system comprising: (a) a microjet injector including: a pressure chamber partially sealed by an elastic membrane and containing a pressure-inducing liquid fluid-tightly filled therein; and a drug chamber adjacent to the pressure chamber, wherein the elastic membrane is disposed between the pressure and drug chambers, wherein the drug solution is contained in the drug chamber, wherein the drug chamber has a micro-nozzle partially defined in a wall thereof for ejecting the drug solution out of the drug chamber; (b) a laser generator for generating a laser beam and emitting the laser beam out of the laser generator, wherein the laser generator is configured by irradiating the laser beam into the pressure-inducing liquid in the microjet injector, thereby generating a bubble in the pressure-inducing liquid; and (c) a fractional laser filter module configured for splitting the laser beam incident from the laser generator into a plurality of fractional laser beams, each beam has a reduced diameter, and for irradiating the fractional laser beams.

In one embodiment of the microjet drug delivery system, the microjet injector and the fractional laser module are detachably and positionally-interchangeably connected to the laser generator, such that the laser beam generated from the laser generator is selectively incident onto and between the microjet injector and the fractional laser module.

In one embodiment of the microjet drug delivery system, the system further comprises (d) a switching unit on which the microjet injector and the fractional laser filter module are mounted, wherein the switching unit is coupled to the laser generator, wherein the switching unit is configured for selectively switching, via user manipulation, between an optical connection between the microjet injector and the laser generator and optical connection between the fractional laser module and the laser generator.

In one embodiment of the microjet drug delivery system, the switching unit includes a switching revolver in a form of a rotatable disc rotating around a central rotation axis, wherein the laser generator is eccentrically coupled to the rotatable disc, wherein a spacing between the microjet injector and the central rotation axis is equal to a spacing between the fractional laser module and the central rotation axis. The rotation of the switching unit may allow the microjet injector and the fractional laser module to be positionally-interchangeably connected to the laser generator, such that the laser beam generated from the laser generator is selectively incident onto and between the microjet injector and the fractional laser module.

In one embodiment of the microjet drug delivery system, the fractional laser module is configured to angularly rotate about a rotation axis parallel to a travel path of the fractional laser beams. According to the rotational configuration of the fractional laser filter module, an inter-perforation spacing defined in the skin may become very small and thus the number of micro-holes per unit area may be drastically increased, thereby to increase the probability that the micro-holes are aligned with the invasion paths of the micro-jets, thereby ensuring a stable drug invasion efficiency.

In one embodiment of the microjet drug delivery system, the laser generator irradiates the laser beam in a focused manner on a point in the pressure-inducing liquid within the pressure chamber. Preferably, the laser generator includes an Er:YAG laser device.

Technical Effects

According to the present disclosure, basically, when using the drug delivery system that administers the drug in the body, invasion of the drug solution into the body may be achieved via ejection of the drug solution in the form of a high-speed microjet instead of injecting the drug directly into the skin using the needle. Thus, the drug delivery system may be realized that can quickly and accurately administer the drug into the body while alleviating the pain during injection.

In particular, according to the microjet drug delivery system in accordance with the present disclosure, prior to the microjet injection, the skin stratum layer was selectively and partially removed by the fractional lasers treatment. Then, administering the drug microjet in the ablated portion while aligning the microjet path thereto may allow the drug to be effectively invaded into the body through the relatively soft skin tissue. Further, the splash-back phenomenon on the skin surface is prevented, thus enabling efficient and reliable drug delivery.

Furthermore, according to the present disclosure, when performing the laser pre-irradiation on the skin to increase the drug delivery efficiency, fractional lasers of micro diameters instead of the non-fractional laser beam are irradiated onto the skin to form micro perforations in the skin. Thus, the skin damage may be reduced and skin regeneration and healing time may be shortened to minimize side effects from the skin laser peeling.

Furthermore, according to a preferred aspect of the present disclosure, configuring the fractional laser filter module to be able to perform the laser perforation in the skin while the fractional laser filter module rotates at a certain angular spacing may allow the positions of the perforated holes in the skin to be distributed in an uniform manner. This greatly increases the number of perforated micro-holes per unit area. Thus, a possibility that the holes defined in the skin by the fractional laser beams may be aligned with the microjet paths may increase. This may be beneficial for the drug to effectively invade into the dermal layer.

BEST MODES FOR INVENTION

Hereinafter, preferred embodiments of a microjet drug delivery device according to the present disclosure will be described in more detail with reference to the accompanying drawings.

Figure 1:
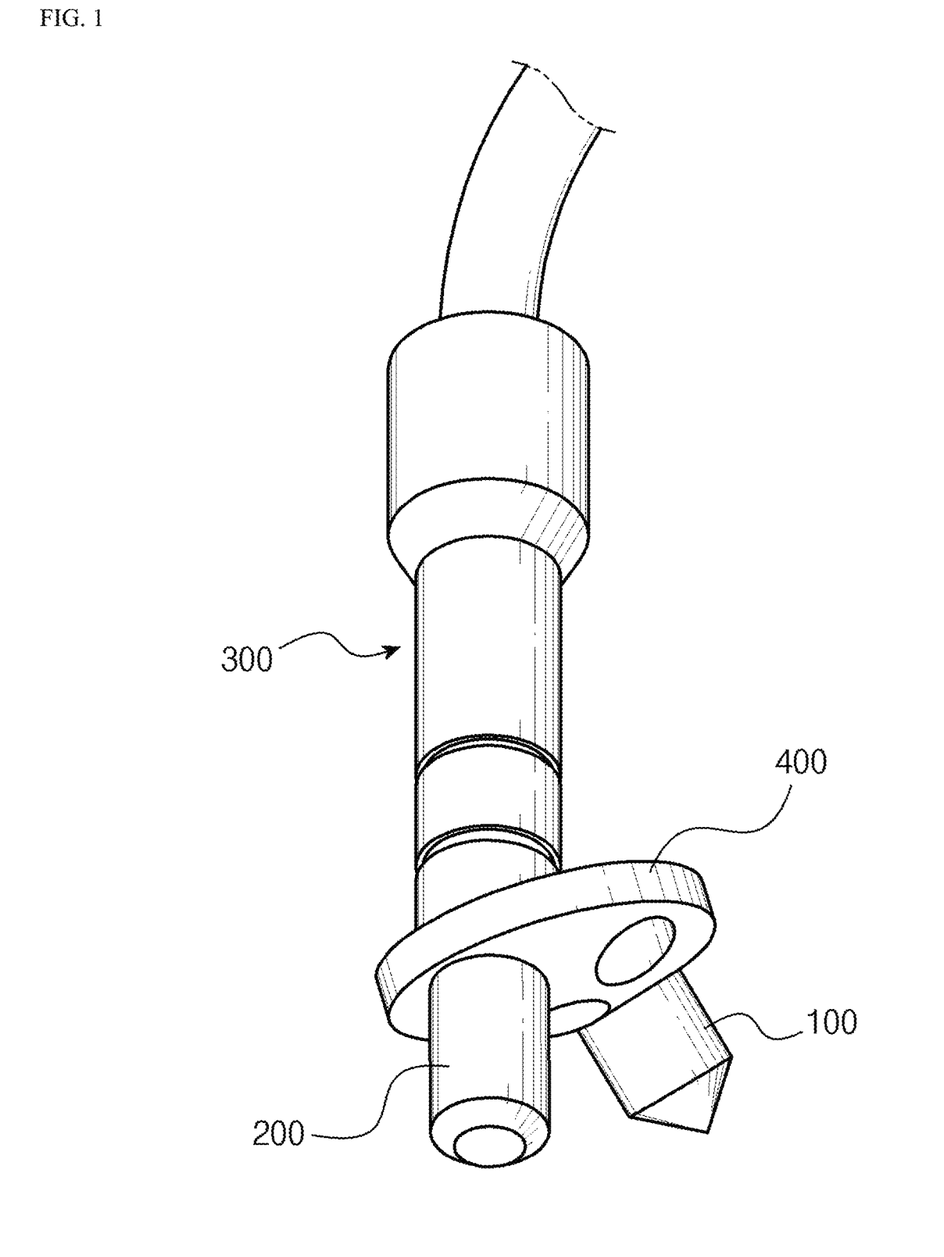
FIG. 1 is a view showing an overall configuration of a microjet drug delivery system according to the present disclosure.

FIG. 1 is a view showing the overall configuration of the microjet drug delivery system according to the present disclosure and a mechanism by which a drug solution is ejected. As shown in FIG. 1, the microjet delivery system according to the present disclosure is configured to generally include a laser generator 300 as a device that generates a laser beam and outputs the same to the outside, a microjet injector 100 as an injection device for storing a drug solution therein at a predetermined volume and administering the solution to the outside in a microjet ejection manner, and a fractional laser filter module 200 for splitting a laser beam incident from the laser generator 300 into fractional laser beams and outputting the fractional laser beams.

Further, according to a main technical feature of the present disclosure, in the microjet drug delivery system in accordance with the present disclosure as described above, the microjet injector 100 and the fractional laser module 200 are detachably and selectively connected to the laser generator 300. As the connection between the microjet injector 100 and the laser generator 300 and the connection between the fractional laser module 200 and the laser generator 300 are switched with each other, a source laser from the laser generator 300 enters either the microjet injector 100 or the fractional laser module 200.

According to the embodiment shown in FIG. 1, the present microjet drug delivery system may include, as a component for switching the connection states of the microjet injector 100 and the fractional laser module 200 to the laser generator 300, a switching unit 400 having a revolver type.

As shown in FIG. 1, the switching unit 400 may have a rotating plate shape capable of rotating about an rotation axis. The microjet injector 100 and the fractional laser module 200 are mounted on the non-central region of the switching unit 400. Further, referring to FIG. 1, the switching unit 400 may be configured as a revolver type structure in which the laser generator 300 is eccentrically coupled to the switching unit 400. Changing the positions of the microjet injector 100 and the fractional laser module 200 on the laser generator 300 may be achieved by rotating the revolver type switching unit 200. Thus, the optical connection states of the microjet injector 100 and the fractional laser module 200 to the laser generator 300 may be switched.

Hereinafter, each of components constituting the microjet delivery system in accordance with the present disclosure as described above will be described in more detail with reference to the attached drawings.

Referring to FIG. 1 showing the microjet drug delivery system according to the present disclosure, the microjet drug delivery system may include the microjet injector 100 as an injection device for storing a drug solution therein at a predetermined volume and administering the solution to the outside in a microjet ejection manner.

Figure 2:
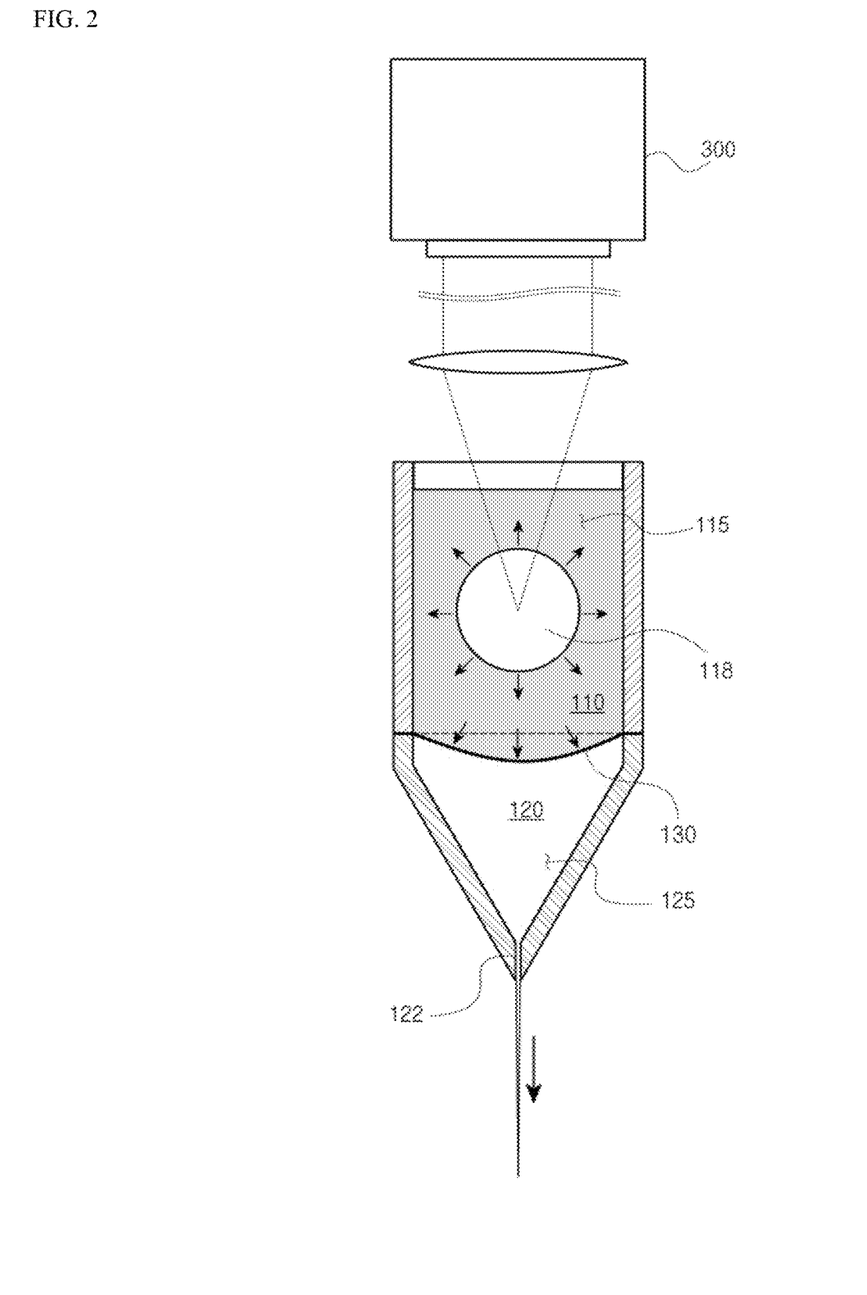
FIG. 2 is a view showing a structure and operating mechanism of a microjet injector as a main component, according to the present disclosure.

FIG. 2 shows a more detailed view of the microjet injector 100. As shown in FIG. 2, according to the present disclosure, the microjet injector 100 is configured to include a pressure chamber 110 filled with a pressure-inducing liquid 115, a drug chamber 120 disposed adjacent to the pressure chamber 110 and containing a drug solution to be ejected therein; and an elastic membrane 130 configured to space between the pressure chamber 110 and the drug chamber 120.

The pressure chamber 110 has an enclosed structure as a whole and has an accommodation space of a certain volume therein. In the interior space thereof, the pressure inducing liquid 115 as a fluid for creating propulsion force is hermetically filled without voids therein. According to the embodiment shown, the pressure chamber 110 may be formed in a substantially cylindrical cylinder shape. The top of the pressure chamber 110 may be made of a transparent material so that the laser beam can pass therethrough. The bottom of the chamber may be configured to be blocked by an elastic membrane 130.

As the pressure inducing liquid 115 filling the inside of the pressure chamber 110, basically, ordinary water may be used. In addition to the water, various liquid materials such as polymers sol and gel, such as alcohol or polyethylene glycol, may also be used as the pressure inducing liquid 115. Further, the pressure inducing liquid 115 may preferably include a degassed liquid for minimizing the residual bubble in the generation of the bubble 115b. Furthermore, the pressure inducing liquid may be prepared by adding an electrolyte (such as salt) to pure water. In this case, since the molecules are ionized and, thus, the energy required for the collapse of the molecular structure of the liquid is small, the bubble may be formed with better efficiency.

The drug chamber 120 is adjacent to the chamber 110 under the pressure chamber 110. The drug solution 125 is stored in the inside of the drug chamber 120. A micro nozzle 140 having a fine diameter is formed in the lower end of the drug chamber 120. As described above, the drug solution 125 may be ejected in the form of a high-speed microjet through the micro nozzle 140 by a propulsion force by which the pressure inducing liquid 115 in the pressure chamber 110 pushes the elastic membrane 130. The diameter of the micro nozzle 140 may be varied according to a desired ejection speed, a target ejection amount, and the like. The diameter may be, for example, in a range of 150 μm or smaller. In one example, although not shown, a drug supply hole may be additionally defined in one side of the drug chamber 120 such that additional drug solution may be supplied thereto from the outside for re-ejection thereof after the ejection of the drug solution 125.

Next, the elastic membrane 130 may be embodied as a thin film having elastic restoring force, and may be disposed between the pressure chamber 110 and the drug chamber 120 to form a boundary therebetween. That is, the pressure chamber 110 and the drug chamber 120 are separated from each other via the elastic membrane 130, and, at the same time, at least one of the pressure chamber 110 and the drug chamber 120 is brought into contact with the elastic membrane 130. Accordingly, when the volume of the pressure inducing liquid 115 in the pressure chamber 110 expands due to the creation of the bubble 115b, the deformation of the elastic membrane 130 may apply pressure to the drug solution 125 in the drug chamber 120.

The elastic membrane 130 may be made of a thin rubber material, preferably a silicone rubber. The silicone rubber not only has excellent stretchability but also has a low thermal conductivity, thereby effectively shielding the heat generated by the laser irradiation and preventing the deterioration and corruption of the drug due to heat transfer. Alternatively, the material of the elastic membrane 130 may employ any material having elasticity and liquid impermeability, depending on the choice of a person skilled in the art. An example of such a material may be nitrile butadiene rubber (NBR).

Figure 3A:
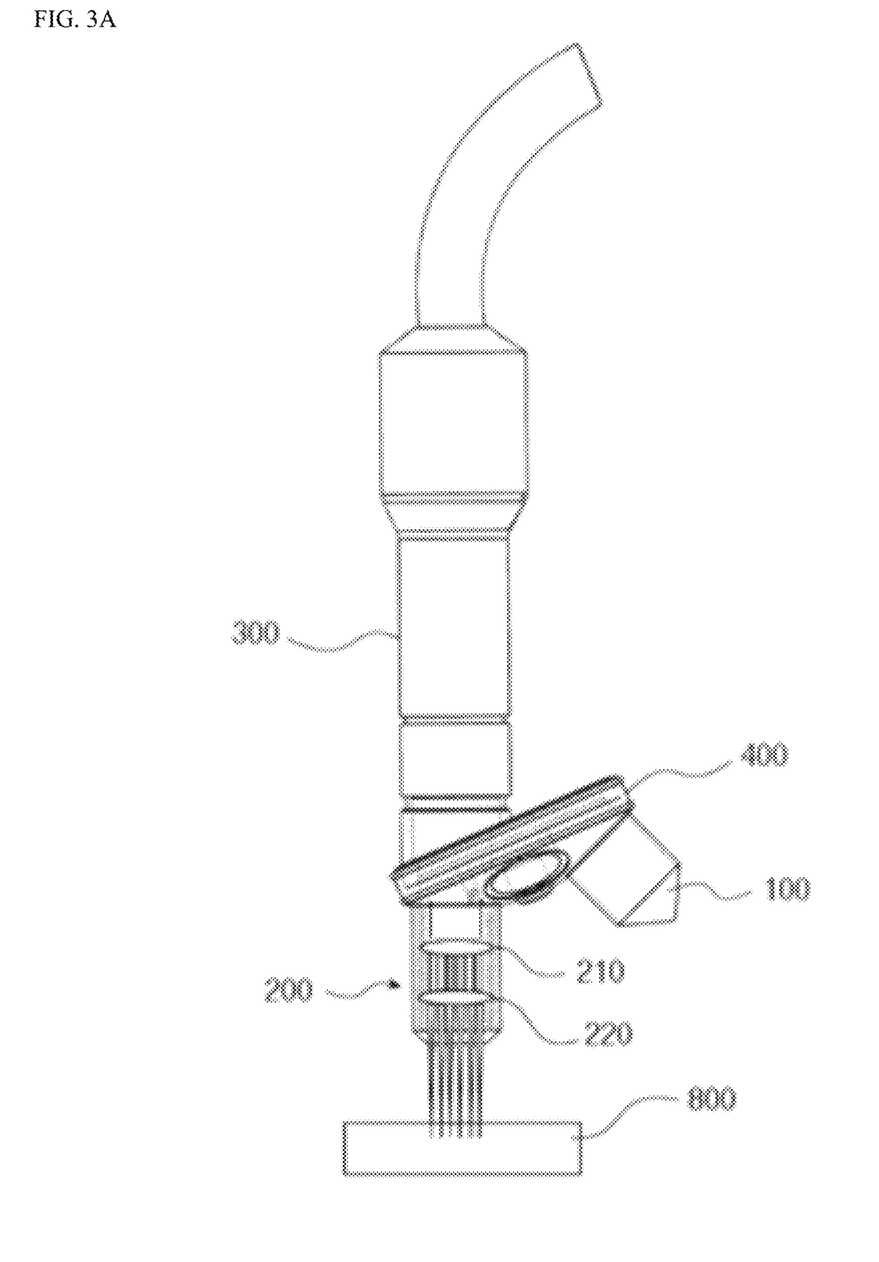
FIGS. 3A and 3B are a view showing a process of microjet injection treatment using the microjet drug delivery system in accordance with the present disclosure.

Next, according to the present disclosure, the fractional laser filter module 200 is embodied as a filter module that splits a laser beam incident from the outside into a plurality of fractional laser beams, each having a micro diameter and outputs the fractional laser beams. The fractional laser filter module 200 includes a pixel beam splitter 210 for splitting a laser beam, as shown in (a) in FIG. 3, and a focusing lens 220 disposed below the pixel beam splitter to condense the split laser beams from the pixel beam splitter 210.

According to a preferred embodiment of the present disclosure, each of the fractional laser beams as output by the fractional laser filter module 200 may in a range of 100 to 200 μm in diameter. An output pattern of the fractional laser beams may be configured, for example, such that, when as a laser generator 300, an Er:YAG laser device (wavelength of 2940 nm) having a 1 J output is employed, the fractional laser beams may be output in a 15×15 grid pattern in an irradiation area of 10 mm×10 mm.

Further, the fractional laser filter module 200 may be fixed, but may be more preferably configured to be rotatable. That is, the fractional laser filter module 200 may be configured to rotate about a rotation axis parallel to a traveling path of the incident source laser beam. While the fractional laser filter module 200 is rotated at a certain angular spacing, the laser is irradiated to the skin. Thus, as shown in FIG. 4, positions of the perforated micro-holes in the skin are not biased but are uniformed distributed, so that the inter-perforation spacing becomes very small and thus the number of micro-holes per unit area may be drastically increased.

Thus, according to the main feature of the present disclosure, following advantages may be achieved. That is, conventionally, in the laser pre-treatment of skin for efficient microjet injection, the micro-holes defined in the skin may not be easily aligned with the microjet invasion paths due to using fractional laser beams. According to the rotational configuration of the fractional laser filter module 200 in accordance with present disclosure, the inter-perforation spacing becomes very small and thus the number of micro-holes per unit area may be drastically increased, thereby to increase the probability that the micro-holes are aligned with the invasion paths of the micro-jets, thereby ensuring a stable drug invasion efficiency.

Figure 4:
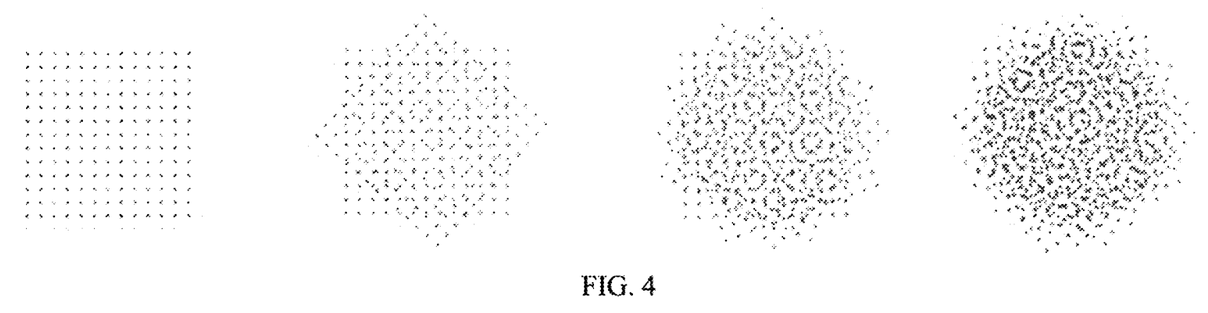
FIG. 4 is a view illustrating increase in the number of micro-holes per unit irradiation area due to rotation of fractional laser beams according to the present disclosure.

In this connection, the rotation angular spacing in the rotation of the fractional laser filter module 200 as described above may be preferably 22.5° angular spacing as illustrated in FIG. 4. Such a rotation angular spacing may be appropriately increased or decreased according to a choice of a person skilled in the art.

The laser generator 300 may be embodied as a laser oscillation device that generates a laser beam. According to the present disclosure, the laser beam emitted from the laser generator 300 is configured to selectively enter a selected one between the microjet injector 100 and the fractional laser filter module 200 as described above. That is, according to the main feature of the present disclosure, the laser generator 300 is first combined with the fractional laser filter module 200 to perform the treatment of the fractional laser beams of the micro-diameter into the skin. Then, the laser generator 300 is disengaged with the fractional laser filter module 200 but is coupled to the microjet injector 100 such that the drug microjet injection is performed using laser bubbles.

According to the present disclosure, as the light source of the laser generator 300, any type of laser may be used without any limitation. For example, various types of laser sources as known in the art, such as Er: YAG laser (wavelength 2.94 μm), Nd: YAG laser (wavelength 1.06 μm), ruby laser, alexandrite laser, Nd: Glass laser, Er: Glass fiber laser, Ho: YAG laser may be employed.

In particular, according to the present disclosure, an Er: YAG laser of wavelength 2940 nm may be most preferably used. The Er: YAG laser is considered in terms of efficiency in selective removal of skin keratin and bubble generation.

The Er: YAG laser has the most favorable wavelength range in terms of absorption into water. Because about 70% of the skin tissue is composed of water, the Er: YAG laser does not invade the skin deeply and is effectively absorbed only into the outermost layer. Thus, the Er: YAG laser is advantageous to selectively remove only the outermost stratum corneum. In addition, when the Er: YAG laser is irradiated into the pressure-inducing liquid 115 in the microjet injector 100, light energy is efficiently absorbed into the liquid. Thus, explosive bubble expansion can be produced, thereby to produce very fast and strong microjets. Accordingly, in view of the above facts, according to the present disclosure, the Er: YAG laser with a wavelength of 2940 nm may be considered to be the most desirable laser source for the laser generator 300.

Next, in accordance with a preferred embodiment of the present disclosure, the switching unit 400 essentially acts to switch between the connection between the microjet injector 100 and the laser generator 300 and the connection between the fractional laser filter module 200 and the laser generator 300. That is, according to the main technical features of the present disclosure, the fractional laser filter module 200 and the microjet injector 100 share the same laser source, that is, a single laser generator 300. The fractional laser filter module 200 and the microjet injector 100 are selectively and optically connected to the laser generator 300 to perform the skin laser treatment and microjet injection selectively. The switching unit 400 may be provided to switch between the optical connections.

Figure 3B:
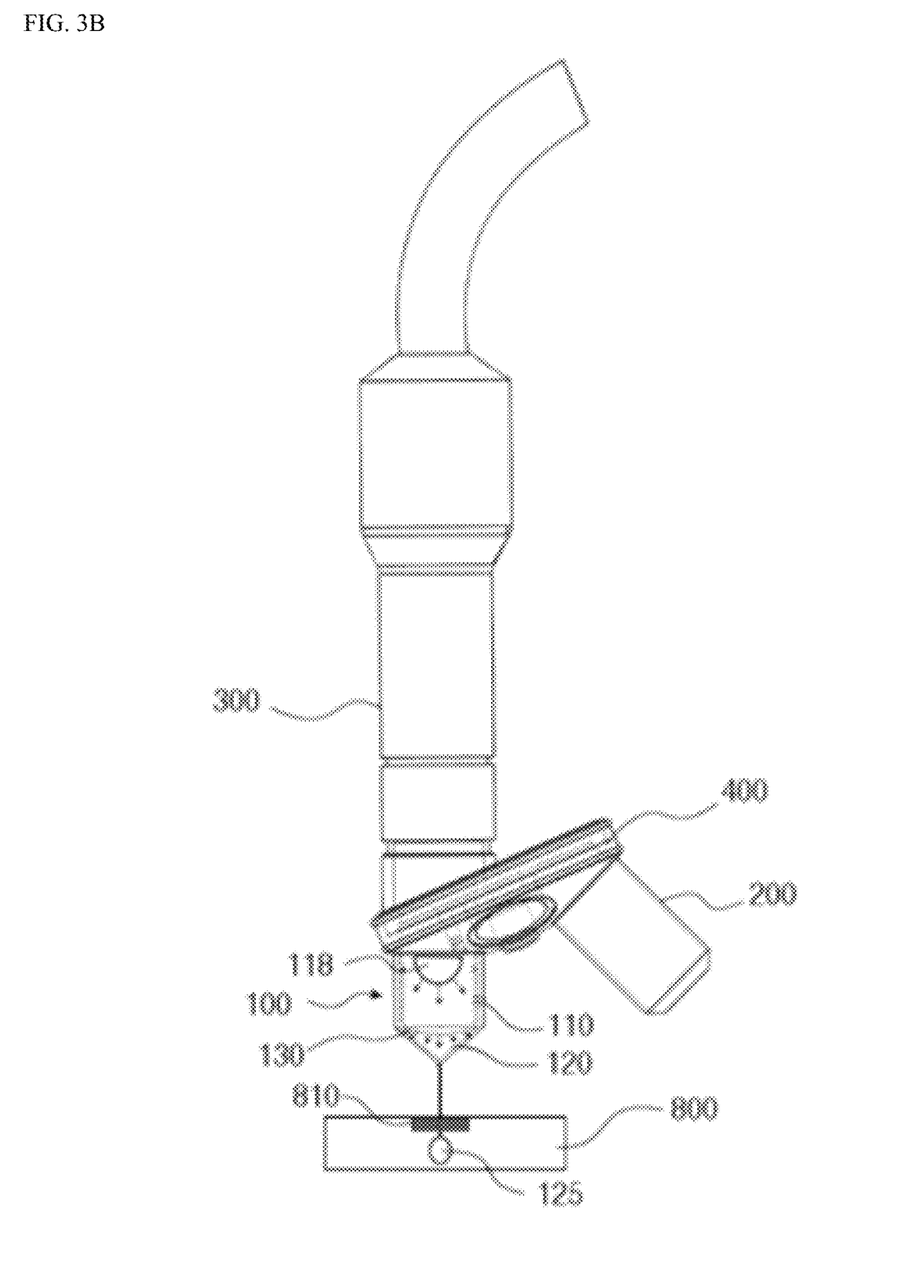

In this connection, the microjet injector 100 and the fractional laser filter module 200 as described above are mounted on the switching unit 400 so that a device to connected to the laser generator 300 may be selected between the microjet injector 100 and the fractional laser filter module 200 via operation of the switching unit 400. Such a switching unit 400 may be preferably implemented in a form of a revolver that rotates about the rotation axis as shown in FIG. 1 and FIG. 3. When the switching unit 400 as described above is connected to the laser generator 300 as shown in FIG. 1 and FIG. 3, the rotation axis is tilted relative to a direction of the laser beam path from the laser generator 300. Thus, when rotating the switching unit 400, the microjet injector 100 and the fractional laser filter module 200 mounted on the non-central region of the switching unit 400 may be sequentially and selectively and optically communicated with the laser generator 300.

Therefore, when using the switching unit 400 of the revolver type as described above, adding the microjet injector 100 and the fractional laser filter module 200 to a tip of a conventional handheld laser device may not increase significantly an overall size of the present system. Further, in use, the user may simply switch the switching unit 400 to switch the optical communications. This is very advantageous for operator convenience.

In one example, in the illustrated embodiment, the revolver type switching unit 400 is illustrated as the most preferred switching unit. The present disclosure is not necessarily limited thereto. The switching unit may be modified into various forms without departing from the essential concept of the present disclosure. For example, the switching unit may be configured to perform the switching operation via horizontal movement of a sliding rail. The switching unit may be designed in various forms according to the choice of a person skilled in the art. In addition, when the switching unit 400 is not provided, the operator may manually switch the connections of the fractional laser filter module 200 and microjet injector 100 to the laser generator 300. Thus, it should be understood that this manual scheme does not depart from the basic technical concept of the present disclosure and therefore falls within the scope of the present disclosure as defined by the claims.

MODES FOR INVENTION

Hereinafter, a microjet injection treatment process using the microjet drug delivery system according to the present disclosure, as configured as described above, will be described in more detail with reference to the accompanying drawings.

FIG. 3 is a view showing the microjet injection treatment process using the microjet drug delivery system according to the present disclosure. As shown in FIG. 3, the treatment process according to the present disclosure may include a first skin ablation (peeling) process and a second microjet injection process.

First, in the treatment process using the microjet drug delivery system in accordance with the present disclosure, the first skin ablation process for preliminarily ablating the skin portion, in particular, the stratum corneum precedes the second microjet injection. In FIG. 3, (a) shows the first skin ablation process.

Referring to FIG. 3, the switching unit of the revolver type 400 on which the fractional laser filter module 200 and the microjet injector 100 are mounted on the tip of the handheld type laser generator 300. Thus, the operator rotates the switching unit 400 to allow the fractional laser filter module 200 to be connected to the laser generator 300 in a straight line. Then, when the laser generator 300 is operated, the laser beam as emitted from the laser generator 300 is incident on the fractional laser filter module 200. Thus, the laser beam as passed through the fractional laser filter module 200 is divided into the fractional laser beams which in turn were irradiated to the skin tissue 800. In the above process, the laser beam as output from the laser generator 300 passes through the pixel beam splitter 210 of the fractional laser filter module 200 as shown in (a) in FIG. 3, and thus is split into a plurality of micro-diameter sized fractional laser beams. Those split fractional laser beams are output through the focusing lens 220 in a condensed form and irradiated to the skin tissue 800.

In this way, the fractional laser beams as irradiated on the skin tissue 800 may perforate micro holes 810, in the stratum corneum of the skin where no nerve layer is present, each hole having a micro-diameter of 100 to 200 μm. In this manner, the skin layer is selectively and partially removed. When of the drug microjets are shot onto the target skin portion in which the micro-holes 810 are perforated, the drug can easily invade the dermis layer through the micro-holes 810.

According to the present disclosure, in this first skin pre-ablation process, instead of irradiating a general laser to the skin to peel an entirety of a certain region of the skin, irradiating the fractional laser beams of the micro-diameter may result in the formation of the micro-holes defined in the certain region of the skin. As a result, a skin tissue around the perforated micro-hole is intact. Thus, skin regeneration and healing time can be greatly shortened compared with the skin peeling of the entirety of the certain region thereof.

However, according to the present disclosure, in performing the microjet injection after the fractional laser beams based skin pre-treatment, it may be difficult to align the invasion paths of the microjets with the skin micro-holes 810. This problem can be effectively solved by a preferred configuration of the present disclosure in which the fractional laser filter module 200 rotates.

That is, according to a preferred aspect of the present disclosure, as described above, the fractional laser filter module 200 may be configured to rotate about a rotational axis parallel to the progress path of the fractional laser beams to be output. Thus, rotating the fractional laser filter module 200 at a certain angular spacing may allow the irradiation direction of the fractional laser beams to be irradiated on the skin to be uniformly changed. Thus, the number of micro-holes per unit area can be greatly increased.

Figure 5:
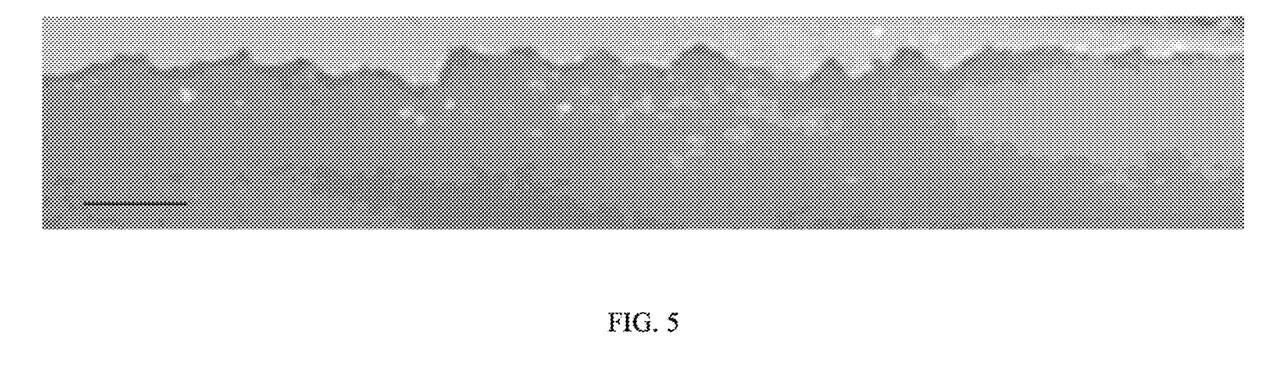
FIG. 5 is a photograph showing an enlarged cross-section of the ablated skin via rotation of the fractional laser beams.
Figure 6A:
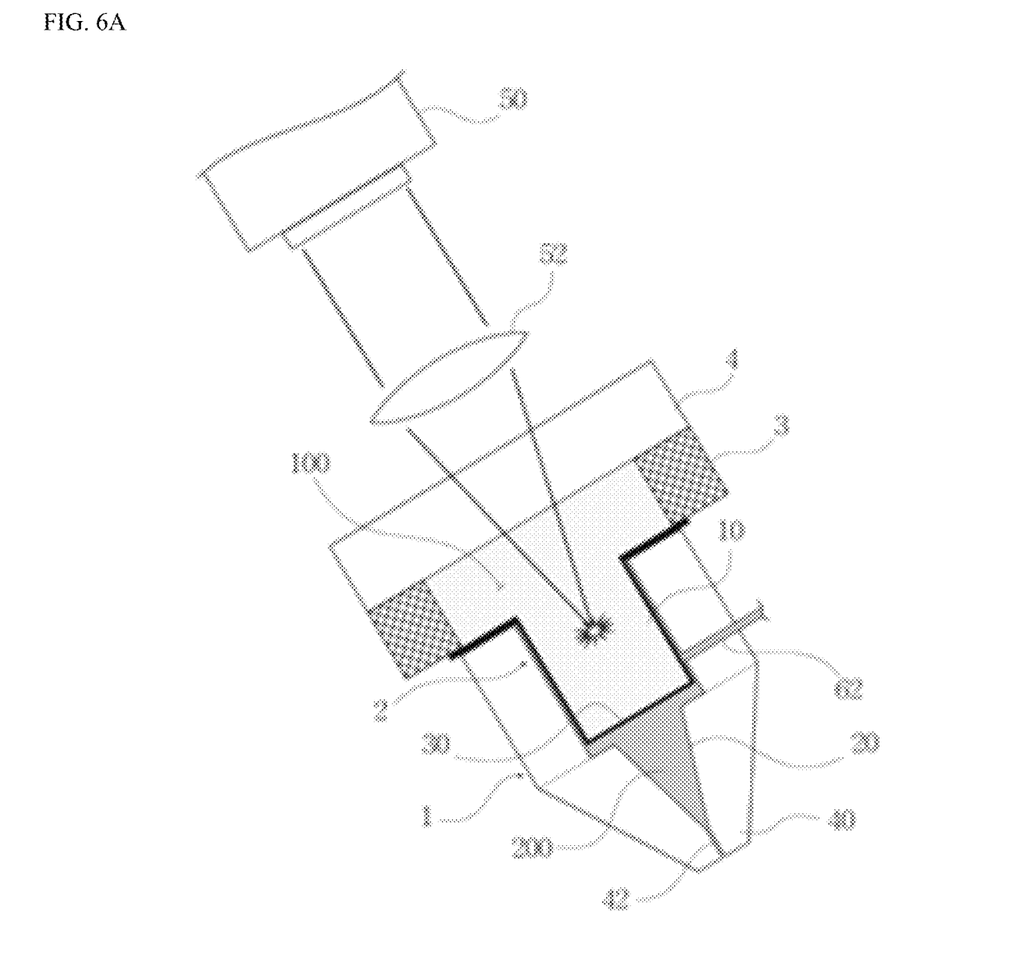
FIGS. 6A and 6B are a view illustrating a structure and principle of a conventional patented laser-bubble based microjet drug delivery device.
Figure 6B:
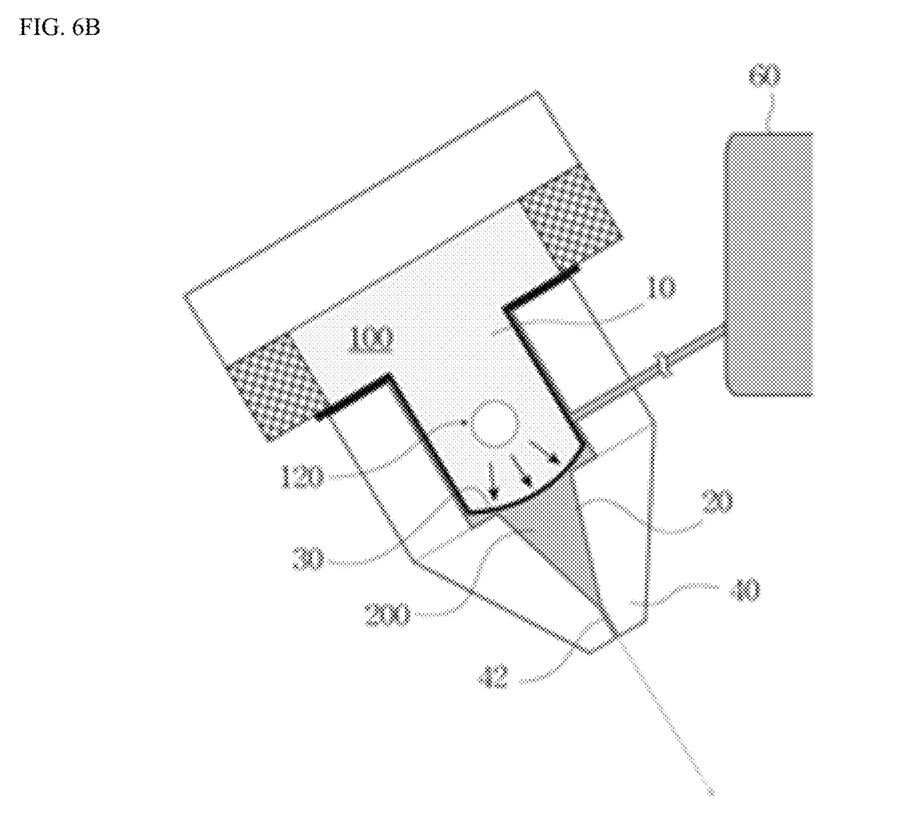

FIG. 4 is a view illustrating the increase in the number of micro-holes per unit irradiation area with rotation of the fractional laser filter module 200. As shown in FIG. 4, it may be seen that when the fractional laser filter module 200 is rotated, the density of the micro holes and the number of the micro holes formed in the skin per each rotation are increased compared to a case when the fractional laser beams are irradiated onto a single spot without the rotation of the fractional laser filter module 200. Thus, the probability of alignment between the drug microjet paths and the micro-holes 810 may be greatly increased, thereby ensuring stable invasion efficiency of the drug. In one example, a sectional view of the skin as ablated by the rotation of the fractional laser filter module 200 is as shown in FIG. 5 where a scale bar at a lower left portion thereof is 1 mm long.

After the first skin ablation process for removing the portion of the stratum corneum using the fractional laser beams as described above, the second microjet injection process as described above is performed in which the drug is administered into the body by ejecting the microjets to the skin target portion in which a certain amount of the stratum corneum of the skin has been removed.

Referring to (b) in FIG. 3, after the completion of the first skin ablation process, the operator rotates the switching unit of the revolver type 400 such that the fractional laser filter module 200 is disconnected from the laser generator 300 and then the microjet injector 100 is connected to the laser generator 300.

When the laser generator 300 is operated while the microjet injector 100 and the laser generator 300 are connected to each other, the laser beam as emitted from the laser generator 300 is condensed into the pressure chamber 110 of the microjet injector 100 to generate bubbles in the pressure-inducing liquid 115 in the pressure chamber 110. The thus-occurring rapid expansion of the bubbles causes the drug solution 125 in the drug chamber 120 to be propelled and ejected in the form of a high-speed microjet through the micro-nozzle 122 toward the skin.

The generation of such microjets will be described in more detail with reference to FIG. 2. Operating the laser generator 300 and irradiating the laser beams, in a focused manner, on the pressure-inducing liquid 115 air-tightly filled in the pressure chamber 100, a phase change of the pressure-inducing liquid 100 occurs upon absorbing of the laser beams such that gas bubbles 118 may be generated in the pressure-inducing liquid 115 as shown in FIG. 2.

As described above, the bubbles 118 as generated in the pressure-inducing liquid 115 rapidly expand instantaneously, and, thus, the internal pressure of the sealed pressure chamber 110 rapidly increases. Thus, the increased internal pressure causes the elastic membrane 130 to expand toward the outside of the pressure chamber 110, that is, toward the drug chamber 120. The elongation deformation of the elastic membrane 130 may allow the drug solution 125 of the adjacent drug chamber 120 thereto may be accelerated via a propulsive force such that the drug solution 125 is released through the micro-nozzle 122 in the form of a high-speed microjet.

The drug microjet thus generated is invaded into the skin through the holes defined in the stratum corneum via the first skin pre-ablation process as described above. In this connection, according to the preferred aspect of this connection the present disclosure, the drug microjets can invade directly into the dermis layer below the stratum corneum at a very high invasion probability without interference by the skin stratum corneum. This can also greatly improve efficiency in the drug delivery.

To check improved performance and effect of the microjet drug delivery system according to the present disclosure as described above, samples in accordance with Present Examples of the present disclosure were prepared and tested. Detailed contents and results thereof are summarized below.

As the laser generator 300, the Er: YAG laser device for emitting laser having a wavelength of 2940 nm, and having a pulse width of 150 μs, a pulse frequency of 10 Hz and an output energy of 1 J/pulse was used. The test was carried out for all following four cases: (1) a case when the microjet is injected without the laser skin ablation; (2) a case when a conventional laser based ablation (18 pulses) and then the microjet injection were conducted; (3) a case when the fractional laser beams based ablation (18 pulses) is followed by the microjet injection; and (4) a case when the fractional laser beams based ablation (18 pulses) together with the rotation of the fractional laser filter module is followed by the microjet injection.

Further, for each of the four cases as described above, in the microjet injection, the laser duration was set to each of 10, 30 and 50 seconds. Then, tissue invasion depth results were compared between the cases. The specific results thereof are shown at Table 1 and a graph of FIG. 8 below. For reference, the results in Table 1 below show comparisons between the case (1) when the microjet is injected without the laser skin ablation and the remaining three cases (2) to (4) in which the laser skin pre-treatment was conducted.

In the case (4) when the fractional laser beams based ablation together with the rotation of the fractional laser filter module is followed by the microjet injection, the rotation of the fractional laser filter module was performed 3 times at a rotation angle of 22.5°.

TABLE 1

| Invasion depth ratios of cases (2) to (4) to case (1) | | | |
|---|---|---|---|
| Cases | 10 s | 30 s | 50 s |
| Case (2): invasion depth ratio of case (2) to case (1) | 1.42 | 1.16 | 1.15 |
| Case (3): invasion depth ratio of case (3) to case (1) | 0.99 | 1.08 | 1.11 |
| Case (4): invasion depth ratio of case (4) to case (1) | 1.33 | 1.13 | 1.16 |

Figure 8:
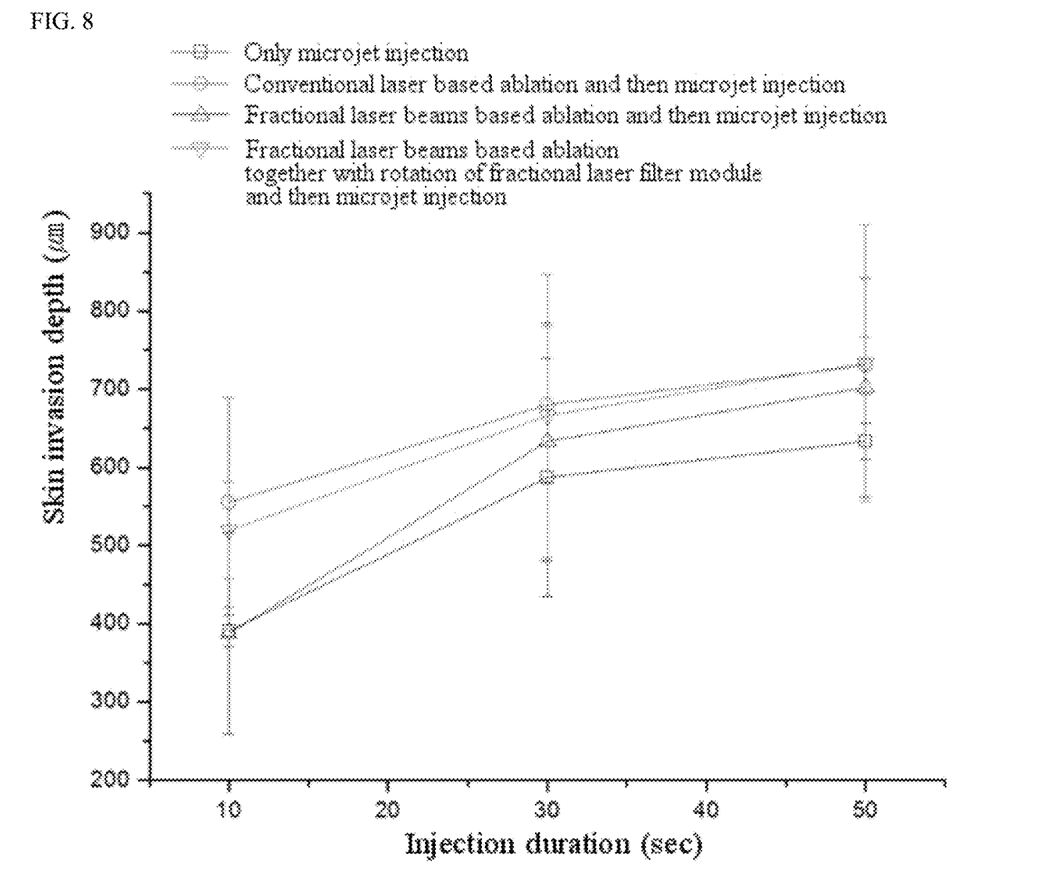
FIG. 8 is a graph showing a tissue invasion depth result in a comparative experiment to confirm the effect of the microjet drug delivery system according to the present disclosure.

As may be seen from the results of Table 1 and FIG. 8, the laser based pre-ablation process prior to the microjet injection may allow the drug invasion depth into the skin tissue to be significantly increased as compared with the case (1) in which only the microjet injection was conducted.

In detail, the case (2) in which the pre-ablation of the skin with the conventional laser beams rather than the fractional laser beams was somewhat effective for each of the laser durations. In the case (4) when the fractional laser beams based ablation together with the rotation of the fractional laser filter module is followed by the microjet injection, the results thereof are comparable to those of the case (2) for each of the laser durations. As for the longer laser injection time, the case (4) is the largest in the invasion depth ratio.

These findings suggest that skin pre-treatment with the fractional laser beams prior to the microjet injection in accordance with the present disclosure leads to a significant improvement in invasion performance as compared to the case when the microjet injection alone is conducted. Especially, according to the desirable aspect of the present disclosure, the improvement of invasion performance was remarkable in the case (4) of the microjet injection after partially ablating the skin while rotating the fractional laser filter module. Thus, the case (4) is most desirable when comprehensively considering side effects from the laser skin ablation and the improvement of invasion performance.

INDUSTRIAL AVAILABILITY

Therefore, according to the present disclosure microjet drug injection device, various medical drugs such as therapeutic drugs, anesthetics, hormones, vaccines, and various kinds of drugs such as cosmetic lotion, tattoo liquid and botulinum toxin (aka Botox) may be injected into human or animal body without pain such that the ejection amount may be accurately adjusted and correct dose may be administered in a repeated manner. Thus, the present device may be particularly advantageously used in various industrial fields such as the medical field, the cosmetic field, the tattoo field, and the livestock field.

What is claimed is:

1. A microjet drug delivery system comprising:
   (a) a microjet injector including:
      a pressure chamber partially sealed by an elastic membrane and containing a pressure-inducing liquid fluid-tightly filled therein; and
      a drug chamber adjacent to the pressure chamber, wherein the elastic membrane is disposed between the pressure and drug chambers, wherein a drug solution is contained in the drug chamber, wherein the drug chamber has a micro-nozzle partially defined in a wall thereof for ejecting the drug solution out of the drug chamber;
   (b) a laser generator for generating a laser beam and emitting the laser beam out of the laser generator, wherein the laser generator is configured by irradiating the laser beam into the pressure-inducing liquid in the microjet injector, thereby generating a bubble in the pressure-inducing liquid;
   (c) a fractional laser filter module configured for splitting the laser beam incident from the laser generator into a plurality of fractional laser beams, each beam has a reduced diameter, and for irradiating the fractional laser beams, and
   (d) a switching unit on which the microjet injector and the fractional laser filter module are mounted, wherein the switching unit is coupled to the laser generator, wherein the switching unit is configured for selectively switching, via user manipulation, between an optical connection between the microjet injector and the laser generator and optical connection between the fractional laser filter module and the laser generator,
   wherein the microjet injector and the fractional laser filter module are detachably and positionally-interchangeably connected to the laser generator, such that the laser beam generated from the laser generator is selectively incident onto and between the microjet injector and the fractional laser filter module.

2. The microjet drug delivery system of claim 1, wherein the switching unit includes a switching revolver in a form of a rotatable disc rotating around a central rotation axis, wherein the laser generator is eccentrically coupled to the rotatable disc, wherein a spacing between the microjet injector and the central rotation axis is equal to a spacing between the fractional laser filter module and the central rotation axis.

3. The microjet drug delivery system of claim 1, wherein the fractional laser filter module is configured to angularly rotate about a rotation axis parallel to a travel path of the fractional laser beams.

4. The microjet drug delivery system of claim 1, wherein the laser generator includes an Er:YAG laser device.

* * * * *